United States Patent [19]

Pearson

[11] Patent Number: 5,077,007

[45] Date of Patent: Dec. 31, 1991

[54] BATCH TREATMENT PROCESS AND APPARATUS FOR THE DISINFECTION OF INFECTIOUS WASTE

[76] Inventor: Erich H. Pearson, 925 Oakwood Ct., Glen Ellyn, Ill. 60137

[21] Appl. No.: 718,633

[22] Filed: Jun. 21, 1991

Related U.S. Application Data

[62] Division of Ser. No. 488,282, Mar. 2, 1990.

[51] Int. Cl.[5] .............................................. G05B 13/00
[52] U.S. Cl. ..................................... 422/3; 210/173; 210/195.3; 210/252; 210/295; 210/513; 210/760; 241/152 R; 241/DIG. 38; 422/28; 422/32; 422/38; 422/140; 422/145; 422/186.07; 422/231; 422/234
[58] Field of Search ................ 422/32, 28, 29, 3, 110, 422/111, 139, 140, 145, 224, 231, 234; 241/21, 24, 29, DIG. 38, 152 R, 152 A; 210/173–174, 760, 765, 194, 195.1, 195.3, 198.1, 199–200, 205–206, 252, 258–260, 294–295, 513, 771, 767, 758, 800, 803, 807

[56] References Cited

U.S. PATENT DOCUMENTS

| 2,246,224 | 6/1941 | Streander | 210/173 |
| 3,549,528 | 12/1970 | Armstrong | 422/28 X |
| 3,772,188 | 11/1973 | Edwards | 210/15 |
| 4,133,638 | 1/1979 | Healey | 422/32 |
| 4,145,007 | 3/1979 | Jetzer | 241/24 |
| 4,178,239 | 12/1979 | Lowther | 210/15 |
| 4,391,413 | 7/1983 | Pack | 241/99 |
| 4,578,185 | 3/1986 | Wilson et al. | 210/85 |

Primary Examiner—Robert J. Warden
Assistant Examiner—Amaha Santiago
Attorney, Agent, or Firm—Donald W. Rupert

[57] ABSTRACT

A process and apparatus for the batch treatment of infectious waste material in a fluidized bed reactor utilizing gas oxidation, preferably ozone gas diluted in air. The process and apparatus provide for the disinfecting of infectious waste in a rapid, cost efficient manner allowing for disposal of such infectious waste material in an environmentally acceptable manner.

15 Claims, 2 Drawing Sheets

BATCH TREATMENT PROCESS AND APPARATUS FOR THE DISINFECTION OF INFECTIOUS WASTE

This is a divisional of application Ser. No. 07/488,282 filed Mar. 2, 1990.

BACKGROUND OF THE INVENTION

1. Field of the Invention

The invention relates to a process and apparatus for the treatment of infectious waste in a rapid, cost efficient manner, with materially less environmental impact than the historically practiced art. More particularly, the invention relates to an apparatus and method for the batch treatment of biologically contaminated medical waste, such as syringes, gowns, bedding, containers, bandages and other liquid or solid materials which may be contaminated with infectious bacterial and viral agents, or with organic contaminants such as chemo-pharmaceuticals, oxidizable solvents, and the like, in a fluidizing bed reactor utilizing gas oxidation.

The disposition of infectious waste is an issue which has received considerable attention among governmental environmental agencies and the public and within the waste disposal industry. Inappropriate disposal practices, as evidenced by infectious medical waste washing up on the beaches of oceans and lakes, as well as being found in ordinary trash containers in public areas, supports the concern that currently practiced treatment and disposal methods are inadequate to handle, in a safe, cost effective manner, the volume of infectious waste being generated today. A process to treat economically large volumes of infectious medical waste in an environmentally acceptable fashion not heretofore used to treat such waste, is therefore needed.

2. Description of the Prior Art

Historically, most infectious waste has been treated by incineration, with the incineration residue thereafter being landfilled or dumped in the oceans. However, recent studies performed on emissions generated from the combustion of medical waste, even from facilities equipped with advanced air pollution control equipment, have demonstrated consistent emission of priority metals, acid gases, and carcinogenic organics such as 2, 3, 7, 8 furans and dioxin. (United States Environmental Protection Agency, *Hospital Waste Combustion Study*, December, 1988). It is the potential toxicity of emissions from medical waste incineration which has driven the capital and operating cost of incineration and pollution control equipment beyond the reach of most hospitals needing to replace old, inefficient, uncontrolled units. Controversy relating to incinerator emissions has also resulted in substantial public opposition to the construction of private or commercial incineration facilities. The consequence has been that demand for the treatment of medical waste has exceeded available supply, and commercial incinerators have, in instances, overcharged the generators of medical waste. This creates an even greater potential for illicit disposal.

Another method traditionally used for decontamination involves steam sterilization in autoclaves. However, autoclaves are not appropriate for economically treating large volumes of infectious waste, and have questionable effectiveness on certain microorganisms. Further, autoclaves do not change the inherent visual appearance of waste, resulting in uncertainty and fear among those persons responsible for its subsequent handling. Many cases have been reported of autoclaved waste being rejected at landfills.

Others have attempted liquid chemical disinfection of medical waste. For instance, U.S. Pat. No. 3,926,379 teaches a continuous process method for the decontamination of solid items of comparatively small size, such as hypodermic syringes. This material is introduced through a feed tube to a hammermill, along with a disinfectant liquid delivered by pump. Pulverized solid waste then drops to a bag or drawer. Disinfectant drains from the bag and is reused. However, with this device, the potential for microbial aerosols exists, as well as the inability to assure that the disinfectant solution has not become neutralized and therefore inactive. Finally, the device is limited to solid, friable objects of small size; it is not suitable for bulk, loose wastes as received from hospitals.

U.S. Pat. No. 4,618,103 discloses a continuous process method for the treatment of solid medical waste by disinfectant fluid during and after introduction to a high speed hammermill. Waste is manually introduced through a rotatable door to a feed tube, and from there to a hammermill along with disinfectant solution. Waste drops to a settling/separation tank, from which disinfectant solution is discharged continuously to a sewer, and solid residue is removed manually As in U.S. Pat. No. 3,926,379, this method appears intended for small, solid objects in limited quantity; it is not therefore suitable for large volumes of medical waste.

U.S. Pat. No. 4,619,409 teaches a continuous process method for the treatment of solid medical waste by disinfectant fluid during and after introduction to a high speed hammermill. Waste material is continuously conveyed to a second conveyor which operates an automatic door ahead of the hammermill. Milled waste drops to a settling/separation tank, from which disinfectant solution is discharged continuously to a sewer, and solid residue is removed manually. As in the previous patents cited above, this method utilizes a high speed hammermill to achieve particle size reduction. Hammermills are suitable when applied to friable materials, but in practice have not proven efficient or effective in achieving particle size reduction with non-friable materials, such as sheet plastic or woven synthetics, neither of which can easily be fractured at standard conditions. Sheet plastics and woven materials comprise a substantial percentage of contaminated medical waste. Further, the method disclosed by this patent is not readily suitable for tonnage quantities of medical waste, owing to the need for manual removal of milled waste from the settling tank, thereby placing humans in contact with the material. Further, as in the previous patents cited above, there is no ability to assure the effectiveness of decontamination on a continuous basis. Finally, as in the previous patents cited, there does not exist the ability to treat other liquid organic wastes typically found among medical waste, for instance chemopharmaceutical materials or solvents, prior to discharge to a municipal sewer.

Applicant's prior U.S. patent application Ser. No. 305,473 discloses an apparatus for the treatment of medical waste on a continuous process basis. However, applicant's prior apparatus is not suitable for gas oxidation using a fluidized bed reactor for the disinfecting of medical wastes, nor is there the ability for improved quality control of the treatment process with applicant's prior apparatus as there is with the batch treatment process of the instant invention.

SUMMARY OF THE INVENTION

It is therefore an object of the present invention to provide an improved waste treatment process which neutralizes bacterial and viral microorganisms, as well as other potentially hazardous organic constituents, in an environmentally acceptable manner.

It is therefore an object of the present invention to provide a waste treatment process for infectious waste on a batch treatment basis, utilizing a fluidized bed reactor vessel, to assure consistent quality control.

It is therefore a further object of the present invention to provide a waste treatment process for infectious waste utilizing gas oxidation as a means to neutralize bacterial and viral microorganisms, as well as other organic constituents. The oxidizer preferably is ozone, delivered to the fluidized bed reactor in the gas phase, neutralizing contaminants as a gas and in partial aqueous solution.

It is therefore an object of the present invention to provide a waste treatment apparatus which neutralizes bacterial and viral microorganisms, as well as other potentially hazardous organic constituents, in an environmentally acceptable manner.

It is a further object of the present invention to provide a waste treatment apparatus for disinfecting infectious waste on a batch treatment basis, utilizing a fluidized bed rector vessel, to assure consistent quality control.

It is a further object of the present invention to provide a waste treatment apparatus for infectious waste utilizing gas oxidation to neutralize bacterial and viral microorganism, as well as other organic constituents. The oxidizer preferably is ozone gas, delivered to the fluidized bed reactor.

The foregoing objects and others are accomplished in accordance with the present invention, by employing the preferred embodiment of the present invention, namely, an apparatus and a method for accomplishing particle size reduction of the infectious waste material and disinfecting the infectious waste material on a batch treatment basis, using gas oxidation, preferably ozone gas, in a fluidized bed reactor process.

These and other objects of the present invention will be apparent from the detailed description given hereinafter. However, it should be understood that the detailed description and specific examples, while indicative of the preferred embodiment of the invention, are given by way of illustration only, because various changes and modifications within the spirit and scope of the invention will become apparent from this detailed description to those skilled in the art.

BRIEF DESCRIPTION OF THE DRAWINGS

For a more complete understanding of this invention, reference should be made to the drawings, as briefly described below.

DETAILED DESCRIPTION OF THE DRAWINGS

Figure 1:
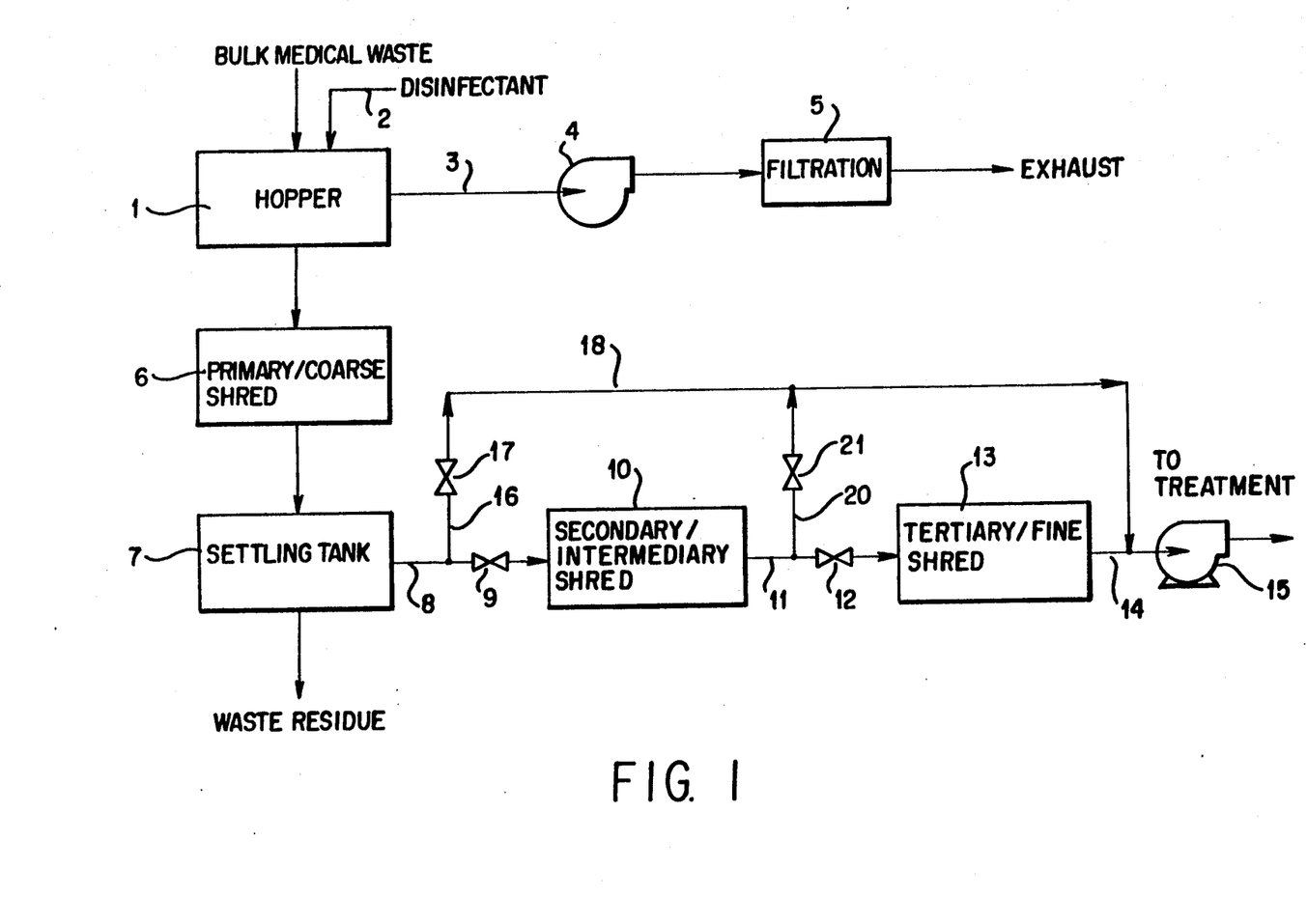
FIG. 1 is a schematic representation of the initial particle size reduction stage of the fluidized bed reactor apparatus and process for the treatment of infectious waste according to the present invention

Referring in detail to FIG. 1, there is illustrated a particle size reduction apparatus and process used to reduce the particle size of the infectious waste material which will subsequently be disinfected using the fluidized bed reactor apparatus and ozone gas oxidation process (shown in detail in FIG. 2).

Referring in detail to FIG. 1, bulk, unseparated infectious waste material (not shown), is manually introduced into a receiving hopper 1, at a nominal rate of 4000 pounds of waste per hour. Disinfectant, which may be a liquid disinfectant such as ozone in aqueous solution, sodium hypochlorite, a hydrogen peroxide solution or any other commercially available disinfectant delivered by a pump (not shown) via pipe 2, is sprayed into receiving hopper 1 to assure that the interior surface of hopper 1 is maintained free of potential bacterial or viral contamination.

Figure 2:
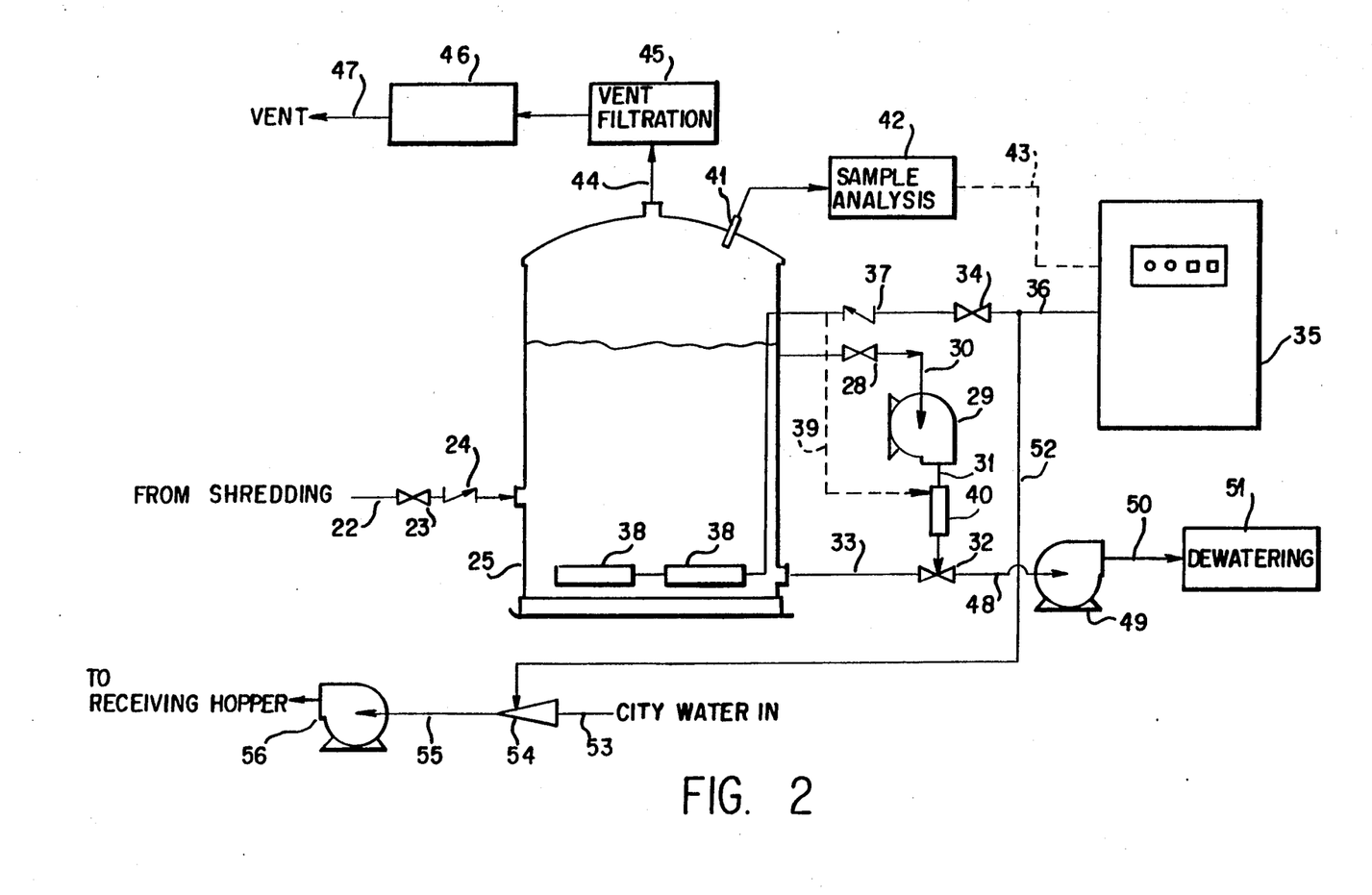
FIG. 2 is a schematic representation of the preferred embodiment of a fluidized bed reactor apparatus and process utilizing gas oxidation for the treatment of infectious waste according to the present invention.

Referring to FIG. 2, if ozone is utilized to disinfect the interior surface of hopper 1, it may be utilized in the following manner. Ozone generator 35 delivers ozone gas through pipes 36 and 52 to eductor 54, a commonly available venturi type diffuser. City water is delivered through pipe 53 to eductor 54, which achieves mass transfer (e.g., transfer of ozone in gas phase to aqueous solution). Other conventional means of achieving mass transfer, such as static inline mixers or ozone reactor towers, may also be used. From eductor 54 dissolved ozone flows through pipe 55 to pump 56, which delivers the dissolved ozone solution to a spray head (not shown) located in receiving hopper 1. This assures that internal hopper surface is maintained free of potential bacterial or viral contamination.

Referring back now in detail to FIG. 1 which illustrates the particle size reduction apparatus and process utilized in the preferred embodiment, air pressure within hopper 1 is maintained lower than air pressure in the facility where the process is being conducted, by inducing air from hopper 1 through duct 3 to blower 4. Air from blower 4 is directed through air filter 5 and is then safely discharged. Air filter 5 consists of a commonly available media type filter (for example fiberglass) to capture particulate which could become entrained in the ventilation stream, plus an activated carbon filter to adsorb any objectionable gases or odors. Negative air pressure within hopper 1 assures that no odor or airborne microorganisms will escape hopper 1.

Waste material is then fed, by gravity, or a motorized conveyor mechanism (not shown), from hopper 1 to a primary shredder 6. Primary shredder 6 may be a low speed, high torque rotary shear shredder, which coarsely shreds the waste material, including metal and glass, and discharges the coarsely shredded waste material into settling tank 7. Settling tank 7 includes a disinfectant solution which is maintained at a predetermined fluid level. The quantity of fluid in settling tank 7 is dependent upon the size and dimensions of the settling tank and must be a level sufficient to allow for separation of large metal waste residue.

Coarsely shredded waste material in settling tank 7 separates by means of gravity so that heavier objects, such as larger pieces of metal, glass, and the like, will settle to the bottom of tank 7. The separation of such larger objects is beneficial so that these objects do not damage or inhibit the operation of subsequent shredding stages.

The coarsely shredded separated waste material which does not readily settle is now in a slurry form, approximately 4-7% solids by weight. This separated waste slurry is induced from settling tank 7 into pipe 8 by transfer pump 15, and through valve 9 into a secondary shredder 10, which reduces waste particles to intermediate size. The waste slurry is further induced by transfer pump 15 to pipe 11, and through valve 12 into a tertiary shredder 13, which further reduces the waste solids to a fine particle size. From tertiary shredder 13 the waste slurry is induced to transfer pump 15 through pipe 14. Pipe 8, valve 9, secondary shredder 10, pipe 11, valve 12, tertiary shredder 13, pipe 14, and transfer pump 15 are flooded, being located below the fluid level maintained in settling tank 7. Secondary shredder 10 and tertiary shredder 13 may be low speed, high torque rotary shear shredders designed for and typically installed in submerged, inline applications.

Efficient particle size reduction of the waste material is necessary to gain maximum surface area for exposure to the disinfectant in the subsequent disinfecting treatment stage shown in FIG. 2. However, secondary shredder 10 and tertiary shredder 13 are optional and may only be required to assure consistent particle size reduction for waste materials which are difficult to shred, such as thin film plastics and some types of woven synthetic materials. Certain other types of waste materials, such as, for example, paper or friable plastics, may not require the additional shredding stages of secondary shredder 10 or tertiary shredder 13.

If primary shredder 6 alone is sufficient to reduce the waste material to an acceptable particulate size, the waste slurry is induced from settling tank 7 to pipe 8; valve 9, valve 21 and/or valve 12, close, and bypass valve 17 opens which allows the flow of waste slurry into pipe 18, and pipe 14, and finally to transfer pump 15 thereby bypassing the shredding stages of secondary shredder 10 and tertiary shredder 13. The waste slurry is then pumped via transfer pump 15 to the disinfecting treatment stage shown in FIG. 2.

Alternatively, if it is determined that primary shredder 6 as well as secondary shredder 10 will be needed to achieve adequate particle size reduction of the waste slurry for disinfection, the waste slurry will be induced into pipe 8 by transfer pump 15; valve 17 will close and valve 9 will open allowing for the waste slurry to enter secondary shredder 10. Valve 12 will close and bypass valve 21 will then open allowing the waste slurry to bypass tertiary shredder 13 and flow into pipe 11, pipe 20, pipe 18, and pipe 14 and finally to transfer pump 15. The waste slurry is then pumped via transfer pump 15 to the disinfecting treatment stage shown in FIG. 2.

Referring now in detail to FIG. 2, there is illustrated the preferred embodiment of the disinfecting treatment apparatus and process utilizing gas oxidation in a fluidized bed reactor apparatus and process.

As shown in detail in FIG. 2, shredded waste, slurry from the shredding apparatus and process shown in FIG. 1, is pumped, via pump 15, at an approximate rate of about 190 GPM (gallons per minute) through pipe 22 and valve 23, and check valve 24 into the fluidized bed reactor vessel 25 until the waste slurry level reaches such a level as has been predetermined given the size of the fluidized bed reactor vessel 25. At this time, the pumping operation ceases and valve 23 closes. Valve 28 then opens and pump 29 starts to recirculate the slurry within tank 25 through pipe 30 on the suction side of the pump 29, pipe 31 on the discharge side of the pump, through three-way valve 32, and through pipe 33 back into tank 25. Once recirculation has been established, valve 34 opens allowing the flow of a gas phase disinfectant/oxidizer, preferably ozone gas, from about 1% to about 1.5% concentration by weight (6035-9053 ppm by volume), and at about 10 psig, to be released from ozone generator 35, into pipe 36 through valve 34 and check valve 37 and delivered to the bottom of fluidized bed reactor vessel 25 through fine bubble diffusers 38. The fine bubble diffusers 38 may be stone diffusers; however, one skilled in the art could appreciate that other diffusion apparatus could be used to achieve the same effect. Alternatively or simultaneously, ozone gas may be directed through pipe 39 to static inline mixer 40. Inline mixer 40 may enhance ozone mass transfer and contact with suspended solids, particularly with higher solids concentrations (e.g., above about 4%). The level of the waste slurry in the fluidized bed reactor vessel 25 during operation of vessel 25 in the disinfecting treatment stage is from about 10% to about 15 percent higher than the level of the waste slurry when vessel 25 is at rest, although the exact height of the waste slurry may vary dependent upon the exact volume of gas delivered through diffusers 38.

Delivery of ozone from about 1% to about 1.5% concentration by weight and 10 psig is typical for commercially available ozone generators producing ozone from oxygen in ambient air. Ozone may also be generated at lower concentrations, and higher concentrations, typically from about 2% to about 4% by weight, if produced from pure gas phase or liquid oxygen However, it is most economical to generate ozone gas from oxygen in ambient air at a concentration of from about 1% to about 1.5% by weight when the disinfecting treatment process of the present invention is employed on a commercial scale. It is well understood that using lower concentrations of ozone will increase the contact time required to destroy bacterial and viral microorganisms, and using higher concentrations of ozone will reduce the necessary contact time. At about 1% ozone concentration by weight entering vessel 25, the disinfecting treatment cycle will take from about 5 to about 45 minutes, depending on the rate of oxidant demand, and on the degree of disinfection desired (e.g., longer contact time for complete microorganism reduction).

The fluidized bed reactor vessel 25, is a sealed vessel. During the disinfecting of the waste material, a sample of the offgas from the operation of fluidized bed reactor 25 is continuously drawn through sample port 41 and analyzed via ozone analyzer 42, which measures residual ozone concentration. A continuous residual ozone concentration of from about 3 to about 5 ppmv in the offgas will assure that oxidant demand will not exceed ozone supply. A control signal transmitted through electrical line 43 to ozone generator 35, regulates the concentration of ozone in order to maintain a continuous residual ozone concentration of from about 3 to about 5 ppmv in the offgas.

Any pressure which could increase within the fluidized bed reactor vessel 25 is relieved through vent pipe 44, filter 45, ozone destruct module 46, and discharge duct 47. Filter 45 may be any commonly available media type air filter, for example fiberglass, to capture particulates which could be entrained in the vent gas. Ozone destruct module 46 is a commonly available unit utilizing catalytic or thermal means to convert ozone to oxygen. Ozone destruct module 46 may also be an activated carbon filter to adsorb ozone.

After the waste slurry has been disinfected, the disinfecting treatment cycle is complete, and valve 34 closes to stop the flow of ozone through pipe 36, check valve 37, and fine bubble diffusers 38, and, alternatively or simultaneously, through pipe 39 to static inline mixer 40. Pump 29 also ceases operation and valve 28 closes, to stop slurry recirculation. Valve 32 then directs the disinfected waste slurry from fluidized bed reactor vessel 25 from pipe 33 to pipe 48, induced by pump 49, which discharges through pipe 50 to dewatering equipment 51. Dewatering equipment 51 may be any of several commonly available liquid-solid separation devices, including, but not limited to centrifuges, belt filters, vacuum filters, filter presses, gravity filters, extruders, and air dryers. After the disinfected waste slurry has been dewatered, the disinfected waste may then be classified for recycling, or is suitable for nonhazardous waste landfill.

In order to further define the specifics of the present invention, the following examples are provided and are intended to illustrate the fluidized bed reactor disinfecting process utilizing gas oxidation of the present invention and not to limit the particulars of the present invention:

EXAMPLE 1

The purpose of this example was to measure bacterial reduction as a function of time and to determine the amount of agitation necessary to limit stratification of the shredded waste material in the fluidized bed reactor vessel.

The waste material to be disinfected consisted of 600 lbs. of water and 18 lbs. of shredded waste solids. The final consistency of the waste material had a solids concentration of 2.9 percent solids by weight. The shredded waste solids constituted approximately 90 weight percent paper and paper products, 9 weight percent plastics, 0.5 weight percent glass and 0.5 weight percent metal.

The shredded waste solids were introduced into a fluidized bed reactor vessel 2.0 feet in diameter and 4.0 feet high. Prior to the introduction of the shredded waste solids, the fluidized bed reactor vessel was filled with city water to 36.75 inches and the water was aerated sufficiently to eliminate any trace amounts of chlorine. The water was then ozonated to neutralize background microorganisms, until an oxidation-reduction potential ("ORP") of 650 millivolts was reached. The water was then additionally aerated to eliminate dissolved ozone. The water remained in the fluidized bed reactor vessel without aerations for 24 hours prior to testing.

After the shredded solid waste material was weighed and introduced into the fluidized bed reactor vessel, the waste slurry was manually agitated for consistent distribution. Samples of approximately 30 ml. were drawn from the bottom and top of the fluidized bed reactor vessel to measure background microorganisms. The samples were drawn by sterile pipette, and placed in sterile 125 ml specimen containers.

Bacteria inoculum was then introduced into the fluidized bed reactor vessel and the waste slurry and inoculum were manually agitated for 5 minutes. The inoculum consisted of 500 ml. of a nutrient broth containing the bacteria species: Bacillus subtilis, Eschericha coli, Pseudomonas aeruoinosa, and Staphylococcus aureus, with a concentration of $1.6'10^5$ per ml. The inoculum was prepared and furnished by an independent microbiological testing laboratory. Once the inoculum was introduced into the waste slurry, samples were drawn from the bottom and top of the fluidized bed reactor vessel using new sterile pipettes for each sample. The samples were placed in sterile 125 ml specimen containers.

The disinfecting cycle was then started. The waste slurry was exposed to ozone gas at 0.3 percent to 0.5 percent ozone concentration by weight diluted in air at approximately 20 CFH and 10 psig. The ozone gas was introduced into the fluidized bed reactor vessel through a single 10 inch porous stone diffuser located at the bottom of the reactor vessel. The waste slurry within the reactor vessel was not agitated during the disinfecting cycle, due to the mechanical failure of the jet aerator/agitator being tested. Samples were drawn from the bottom and top of the reactor vessel in 5 minute intervals for a total time of 60 minutes during the disinfecting cycle. Each sample was drawn with a new sterile pipette and placed in a sterile specimen container.

A total of 16 sealed specimen containers were returned to an independent microbiological testing laboratory for incubation and plate counts. Consistent distribution of solids in suspension in the reactor vessel was not achieved due to the failure of the agitation device. The diffuser stone generated a vortex, but much of the waste material was not moved away from the sides of the vessel at any time.

The results shown in Table I indicate that this run generated an approximate 66% reduction in bacterial concentration within five minutes No further reduction was achieved. Although bacterial concentrations were not sufficiently reduced, the results showed that the biocidal mechanism for ozone is contact and dosage dependent, and not time dependent as it is for chlorinated bactericides.

TABLE I

| RUN | TIME (Minutes) | PLATE COUNT (Organisms/ml.) | SOLIDS % | $O_3$ % | CFH |
| --- | --- | --- | --- | --- | --- |
| 1 | Background | $1.5 \times 10^5$ | 2.9 | 0.5 | 20 |
|  | Inoculation | $1.3 \times 10^5$ |  |  |  |
|  | 5-T (1) | 45,000 |  |  |  |
|  | 5-B (2) | 50,000 |  |  |  |
|  | 10 T | 47,000 |  |  |  |
|  | 10-B | 47,000 |  |  |  |
|  | 15-T | 47,000 |  |  |  |
|  | 15-B | 55,000 |  |  |  |
|  | 20 T | 45,000 |  |  |  |
|  | 20-B | 47,000 |  |  |  |
|  | 25-T | 45,000 |  |  |  |
|  | 25 B | 31,000 |  |  |  |
|  | 30-T | 45,000 |  |  |  |
|  | 30-B | 47,000 |  |  |  |
|  | 35-T | 35,000 |  |  |  |
|  | 35-B | 47,000 |  |  |  |
|  | 40-T | 39,000 |  |  |  |
|  | 40-B | 37,000 |  |  |  |
|  | 45-T | 39,000 |  |  |  |
|  | 45-B | 48,000 |  |  |  |
|  | 50-T | 50,000 |  |  |  |
|  | 50-B | 47,000 |  |  |  |
|  | 55-T | 41,000 |  |  |  |
|  | 55-B | 45,000 |  |  |  |
|  | 60-T | 40,000 |  |  |  |
|  | 60-B | 43,000 |  |  |  |

Notes: (1) T = samples drawn from top of liquid surface in the reactor vessel.
(2) B = samples drawn from bottom of reactor vessel.

EXAMPLE 2

The purpose of this example was to measure bacterial reduction as a function of time.

The waste material to be disinfected consisted of 600 lbs. of water and 18 lbs. of shredded waste solids having the composition of Example 1. Reactor vessel dimensions and preparation were identical to Example 1. The reactor vessel was equipped with a mechanical agitator Inoculum was introduced to the reactor and agitated with a motorized paddle type mechanical agitator for five minutes. The inoculum consisted of 500 ml of nutrient broth with bacteria types identical to those used for Example 1, with a concentration of $1 \times 10^5$ per ml. The mechanical agitator was operated for the duration of the test run.

Samples of the waste slurry were drawn by pipette from a point approximately 1'-0" beneath the liquid surface in the reactor vessel. The waste slurry was exposed to ozone gas at about 1% by weight diluted in air at approximately 10 CFH and 10 psig.

Samples were drawn at one minute intervals for the first five minutes of treatment to develop a population reduction curve for that interval. A total of twelve samples were drawn: one background, one inoculation, one at each one minute interval for the first five minutes, and one for each five minute interval to thirty minutes.

At the end of the sampling run, it was discovered that the ozone generator had failed (no ozone in the delivery of compressed air). It was not known at what point during the test run the generator failed. Samples were returned to the independent microbiological testing laboratory for incubation and plate counts. Results shown in Table II suggest that the ozone generator failed at the start of the test run, as no bacterial reduction was achieved. Because background and inoculation counts were statistically equivalent, cross contamination is suspected: pipettes used for Example 1 were washed in sodium hypochlorite and thoroughly rinsed, and reused for Example 2. These results suggest that the pipettes may have been contaminated. Therefore, only sterile implements were used for future sampling.

TABLE II

| RUN | TIME (Minutes) | PLATE COUNT (Organisms/ml.) | SOLIDS % | O₃ % | CFH |
| --- | --- | --- | --- | --- | --- |
| 2 | Background | 900,000 | 2.9 | 0 | 10 |
|   | Inoculation | 910,000 |     |   |    |
|   | 1 | 900,000 |     |   |    |
|   | 2 | 910,000 |     |   |    |
|   | 3 | 910,000 |     |   |    |
|   | 4 | 930,000 |     |   |    |
|   | 5 | 930,000 |     |   |    |
|   | 10 | 930,000 |     |   |    |
|   | 15 | 920,000 |     |   |    |
|   | 20 | 900,000 |     |   |    |
|   | 25 | 910,000 |     |   |    |
|   | 30 | 900,000 |     |   |    |

EXAMPLE 3

The purpose of this example was to measure bacterial reduction as a function of time, in an environment having a lower concentration of paper pulp to establish baseline performance. In this Example, a solids handling pump was used for recirculation of the shredded waste slurry.

The waste material to be disinfected consisted of approximately 30% of the waste slurry used in Example 2, the balance of which had been manually removed from the fluidized bed reactor vessel. The water level in the reactor vessel was then raised to 36.75 inches with city water. The slurry was ozonated to reduce background microorganisms until an ORP of 650 mV was reached. The slurry was left at rest for 24 hours to reduce residual chlorine and to permit dissolved ozone to decompose.

Inoculum used for this test run consisted of 500 ml of nutrient broth with bacterial species identical to the previous examples, with a concentration of $1 \times 10^5$ per ml. As in previous examples, inoculum was prepared by an independent microbiological testing laboratory.

A solids handling, air operated, double diaphragm pump was used to recirculate the waste slurry, to limit stratification. The pump was operated for five minutes, and a sample was drawn by sterile pipette to measure background microorganisms. The inoculum was then introduced and recirculated, and the inoculum sample drawn.

Diluted ozone at 1% by weight, 10 CFH and 10 psig was then introduced into the reactor vessel by a porous stone diffuser located at the bottom of the reactor vessel. Samples were drawn at one minute intervals for the first five minutes, and at five minute intervals to forty minutes. All samples of the waste slurry were placed in sterile 125 ml specimen containers, and returned to the independent microbiological testing laboratory for incubation and plate counts. The results of this example, shown in Table III, indicate that bacterial populations were reduced below detectable levels between five and ten minutes, during an interval that samples were not drawn.

TABLE III

| RUN | TIME (Minutes) | PLATE COUNT (Organisms/ml.) | SOLIDS % | O₃ % | CFH |
| --- | --- | --- | --- | --- | --- |
| 3 | Background | <10 | <2 | 1 | 10 |
|   | Inoculation | 70,000 |    |   |    |
|   | 1 | 100,000 |    |   |    |
|   | 2 | 65,000 |    |   |    |
|   | 3 | 30,000 |    |   |    |
|   | 4 | 25,000 |    |   |    |
|   | 5 | 10,000 |    |   |    |
|   | 10 | <10[1] |    |   |    |
|   | 15 | <10 |    |   |    |
|   | 20 | <10 |    |   |    |
|   | 25 | <10 |    |   |    |
|   | 30 | <10 |    |   |    |
|   | 35 | <10 |    |   |    |
|   | 40 | <10 |    |   |    |

NOTE: [1]A plate count of <10 organisms per ml. represents the lower limit of detectability for quantitative testing.

EXAMPLE 4

The purpose of this example was to measure bacterial reduction as a function of time, using elevated bacterial concentrations; to test alternative reactor vessel geometry, intended to enhance ozone mass transfer; and also to establish baseline performance for alternate vessel geometry by testing low solids concentration.

The rate of ozone mass transfer to water is a function of several variables, principal among which are bubble surface area relative to volume and bubble retention. Bubble size was not modified for this run since common stone diffusers were employed for the screenings. However, vessel geometry was modified to increase bubble retention, to duplicate more accurately retention for a commercial scale treatment process. Retention was increased by increasing SWD, (side water depth) to 14 feet, in a vessel 12" diameter and 17'-0" high. Without agitation or recirculation, bubble retention would be approximately 14 seconds (e.g., 1 ft/sec. rise for 1 mm bubbles), which is nominally required for mass transfer of reasonable efficiency. Recirculation, to limit stratification, was achieved with a solids handling, air operated, double diaphragm pump.

684 pounds of water was required to reach 14'-0" SWD. The waste solids concentration in this example was approximately 1.2% by weight. The waste slurry was ozonated to 650 mV the day preceding this test run to reduce background microorganisms. The reactor vessel was also left at rest to eliminate trace chlorine and to allow dissolved ozone to decompose.

Samples of waste slurry were drawn through a ¾" gate valve located at the discharge of the recirculation pump. The valve was left partially open to continuously flush approximately 200 cc/min. of waste slurry to assure accurate sampling. All samples were placed in sterile 125 ml specimen containers.

The pump was operated for five minutes, and a sample drawn for measurement of background microorganisms. Inoculum consisting of the identical bacterial species were used, at a bacterial concentration of $1 \times 10^7$ per ml, which was approximately one hundred times greater than for previous test examples.

Diluted ozone was injected through a porous diffuser at the bottom of the reactor vessel at 1% by weight, 10 CFH, and 10 psig. Samples were drawn at one minute intervals for ten minutes after the start of the ozone generator.

The results shown in TABLE IV indicate a reduction of bacterial population below detectability between nine and ten minutes of treatment with ozone.

TABLE IV

| RUN | TIME (Minutes) | PLATE COUNT (Organisms/ml.) | SOLIDS % | $O_3$ % | CFH |
|---|---|---|---|---|---|
| 4 | Background | <10 | <2 | 1 | 10 |
|   | Inoculation | $3.1 \times 10^6$ | | | |
|   | 1 | $5.0 \times 10^6$ | | | |
|   | 2 | $3.1 \times 10^6$ | | | |
|   | 3 | $2.5 \times 10^6$ | | | |
|   | 4 | 70,000 | | | |
|   | 5 | 50,000 | | | |
|   | 6 | 2,300 | | | |
|   | 7 | 750 | | | |
|   | 8 | 210 | | | |
|   | 9 | 270 | | | |
|   | 10 | <10 | | | |

EXAMPLE 5

The purpose of this example was to measure bacterial reduction as a function of time, with a higher concentration of waste solids than that used in Example 4.

The concentration of waste solids for Example 5 was 4.9% by weight in 684 pounds of water. SWD was 14'-0", and a solids handling, air operated, double diaphragm pump was used for recirculation to limit stratification. The reactor vessel geometry was identical to that used in Example 4. The inoculum composition was identical to that for previous examples; bacterial concentration was over $10^6$/ml.

The waste slurry in the reactor vessel was ozonated to 650 mv the day prior to the test to reduce background microorganisms. The slurry was left at rest for 24 hours to eliminate trace chlorine and to allow dissolved ozone to decompose.

Samples of the waste slurry were drawn through a ¾ gate valve at the discharge side of the diaphragm pump. The valve was left partially open to flush approximately 200 cc/min., to assure accurate sampling. All samples were placed in sterile 125 ml specimen containers, and returned to the independent microbiological testing laboratory for incubation and plate counts.

Samples were drawn at one minute intervals for ten minutes, and at five minute intervals until a thirty minute total processing interval had elapsed.

The results as shown in TABLE V indicate a 99.97% reduction in bacterial organisms within ten minutes of treatment with ozone, and a reduction below detectability within twelve minutes.

TABLE V

| RUN | TIME (Minutes) | PLATE COUNT (Organisms/ml.) | SOLIDS % | $O_3$ % | CFH |
|---|---|---|---|---|---|
| 5 | Background | 8,000 | 4.9 | 1 | 10 |
|   | Inoculation | 730,000 | | | |
|   | 1 | $2.1 \times 10^6$ | | | |
|   | 2 | 950,000 | | | |
|   | 3 | 300,000 | | | |
|   | 4 | 400,000 | | | |
|   | 5 | 170,000 | | | |
|   | 6 | 110,000 | | | |
|   | 7 | 3,100 | | | |
|   | 8 | 2,000 | | | |
|   | 9 | 1,300 | | | |
|   | 10 | 700 | | | |
|   | 11 | 90 | | | |
|   | 12 | <10 | | | |

TABLE VI shown below sets forth a tabulation of the results for Examples 3, 4, and 5. TABLE VI indicates that a 99 percent kill rate of bacteria was achieved after treating contaminated waste slurry with diluted ozone gas for between 5 to 10 minutes. The data shown in Table VI were normalized to the highest measured plate count for each example.

TABLE VI

| TIME (Minutes) | EXAMPLE 3 % Kill Rate | EXAMPLE 4 % Kill Rate | EXAMPLE 5 % Kill Rate |
|---|---|---|---|
| Inoculation | — | — | — |
| 1 | 0 | 0 | 0 |
| 2 | 35.0000 | 38.0000 | 54.7619 |
| 3 | 70.0000 | 50.0000 | 85.7143 |
| 4 | 75.0000 | 98.6000 | 80.9524 |
| 5 | 90.0000 | 99.0000 | 91.9048 |
| 6 | n.o. (1) | 99.9540 | 94.7619 |
| 7 | n.o. | 99.9850 | 99.8524 |
| 8 | n.o. | 99.9958 | 99.9048 |
| 9 | n.o. | 99.9946 | 99.9381 |
| 10 | >99.9900 | >99.9998 | 99.9667 |
| 11 | n.o. | | 99.9957 |
| 12 | n.o. | | >99.9995 |
| 15 | >99.9900 | | |
| 20 | >99.9900 | | |
| 25 | >99.9900 | | |
| 30 | >99.9900 | | |
| 35 | >99.9900 | | |
| 40 | >99.9900 | | |

NOTE: (1) n.o. = not observed

What is claimed is:

1. An apparatus for the treatment of infectious waste material, comprising:
   a bulk waste input means for receiving infectious waste material;
   a decontamination means connected to said bulk waste input means, for decontaminating the surfaces of said bulk waste input means;
   at least one disintegrator means associated with said bulk waste input means, for reducing the particle size of the infectious waste material;
   a separating means connected to said disintegrator means, for separating reduced waste material from waste residue, said separating means capable of receiving fluid for filling to a predetermined fluid level;

a disinfecting means including: (1) a tank means disposed in a position to receive the infectious waste material from said separating means; (2) a disinfectant generating means connected with said tank means, which continuously generates a disinfectant; (3) an agitation analyzing means associated with said tank means and connected with said disinfectant generating means, wherein said analyzing means continuously monitors the amount of disinfectant utilized in said tank means and meters the amount of disinfectant generated from said disinfectant generating means; and dewatering means associated with said disinfecting means, which removes solid, disinfected waste material from liquid residue.

2. An apparatus for the treatment of infectious waste material according to claim 1, wherein said disintegrator means comprises a primary shredding means connected to said bulk waste input means, for reducing the particle size of the infectious waste material.

3. An apparatus for the treatment of infectious waste material according to claim 1, wherein said disintegrator means comprises a primary shredding means connected to said bulk waste input means, for reducing the particle size of the infectious waste material; and a secondary shredding means connected to said separating means, which further reduces the particle size of the infectious waste material.

4. An apparatus for the treatment of infectious waste material according to claim 1, wherein said disintegator means comprises a primary shredding means connected to said bulk waste input means, for reducing the particle size of the infectious waste material; a secondary shredding means connected to said separating means, which further reduces the particle size of the infectious waste material; and a tertiary shredding means connected with said secondary shredding means, which still further reduces the particle size of the infectious waste material.

5. An apparatus for the treatment of infectious waste material according to claim 2, 3 or 4, wherein said primary shredding means is a rotary shear shredder.

6. An apparatus for the treatment of infectious waste material according to claim 3 or 4, wherein said secondary shredding means is a rotary shear shredder, said secondary shredder being in liquid communication with said separating means and disposed below said fluid level of said separating means.

7. An apparatus for the treatment of infectious waste material according to claim 4, wherein said tertiary shredding means is a rotary shear shredder, said tertiary shredder being in liquid communication with said secondary shredder and disposed below said fluid level of said separating means.

8. An apparatus for the treatment of infectious waste material according to claim 1, wherein said separating means is a settling tank having a predetermined fluid level sufficient to gravitationally separate the reduced waste material from waste residue.

9. An apparatus for the treatment of infectious waste material according to claim 1, wherein said agitation means of said tank means is a fluidized bed reactor means.

10. An apparatus for the treatment of infectious waste material according to claim 9, wherein said fluidized bed reactor means includes a diffusing means for releasing disinfectant produced from said disinfectant generating means into said fluidized bed reactor means; a venting means for relieving pressure within said fluidized bed reactor means; a recirculation port means to allow said waste slurry to be recirculated throughout said fluidized bed reactor means; a sample port means for drawing a sample of off gas from said fluidized bed reactor means, said sample port means being connected with said analyzing means; and a discharge port means to allow said waste slurry to be removed from said fluidized bed reactor means.

11. An apparatus for the treatment of infectious waste material according to claim 1, wherein said disinfectant generating means is an ozone generator.

12. An apparatus for the treatment of infectious waste material according to claim 1, wherein said disinfectant is ozone gas at from about to about 1.5 percent concentration by weight diluted in air at 10 psig.

13. An apparatus for the treatment of infectious waste material, comprising:

a bulk waste input means for receiving infectious waste material;

a decontamination means connected to said bulk waste input means, for decontaminating the surfaces of said bulk waste input means;

a primary rotary shear shredder associated with said bulk waste input means, for reducing the particle size of the infectious waste material;

a settling tank connected to said primary shredder for separating reduced waste material from waste residue, said settling tank capable of receiving fluid for filling to a predetermined fluid level sufficient to gravitationally separate the reduced waste material from waste residue;

a fluidized bed reactor disposed in a position to receive the infectious waste material from said settling tank, said fluidized bed reactor having (1) a diffusing means for releasing diluted ozone gas produced from an ozone generator into said fluidized bed reactor; (2) a venting means for relieving pressure within said fluidized bed reactor; (3) recirculation port means to allow said waste slurry to be recirculated throughout said fluidized bed reactor, (4) a sample port means for drawing a sample of off gas from said fluidized bed reactor, said sample port being interconnected with an analyzing means; and (5) a discharge port means to allow said waste slurry to be removed from said fluidized bed reactor;

an ozone generator connected with said fluidized bed reactor, which continuously generates ozone gas at from about 1 to about 1.5 percent concentration by weight diluted in air at 10 psig., for about 5 to about 45 minutes;

an agitation means associated with said fluidized bed reactor;

an analyzing means associated with said fluidized bed reactor and connected with said ozone generator, wherein said analyzing means continuously monitors the amount of diluted ozone gas utilized in said fluidized bed reactor and meters the amount of diluted ozone gas generated by said ozone generator; and dewatering means associated with said fluidized bed reactor, which removes solid, disinfected waste material from liquid residue.

14. An apparatus for the treatment of infectious waste material, comprising:

a bulk waste input means for receiving infectious waste material;

a decontamination means connected to said bulk waste input means, for decontaminating the surfaces of said bulk waste input means;

a primary rotary shear shredder associated with said bulk waste input means, for reducing the particle size of the infectious waste material;

a settling tank connected to said primary shredder for separating reduced waste material from waste residue, said settling tank capable of receiving fluid for filling to a predetermined fluid level sufficient to gravitationally separate the reduced waste material from waste residue;

a secondary rotary shear shredder, connected to said settling tank, which further reduces the particle size of the infectious waste material, said secondary shredder being in liquid communication with said settling tank and disposed below said fluid level of said settling tank;

a fluidized bed reactor disposed in a position to receive the infectious waste material from said settling tank, said fluidized bed reactor having (1) a diffusing means for releasing diluted ozone gas produced from an ozone generator into said fluidized bed reactor; (2) a venting means for relieving pressure within said fluidized bed reactor; (3) recirculation port means to allow said waste slurry to be recirculated throughout said fluidized bed reactor; (4) a sample port means for drawing a sample of off gas from said fluidized bed reactor, said sample port being connected with an analyzing means; and (5) a discharge port means to allow said waste slurry to be removed from said fluidized bed reactor;

an ozone generator connected with said fluidized bed reactor, which continuously generates ozone gas at from about 1 to about 1.5 percent concentration by weight diluted in air at 10 psig., for about 5 to about 45 minutes;

an agitation means associated with said fluidized bed reactor;

an analyzing means associated with said fluidized bed reactor and connected with said ozone generator, wherein said analyzing means continuously monitors the amount of diluted ozone gas utilized in said fluidized bed reactor and meters the amount of diluted ozone gas generated from said ozone generator; and dewatering means associated with said fluidized bed reactor, which removes solid, disinfected waste material from liquid residue.

15. An apparatus for the treatment of infectious waste material, comprising:

a bulk waste input means for receiving infectious waste material;

a decontamination means connected to said bulk waste input means, for decontaminating the surfaces of said bulk waste input means;

a rotary shear shredder associated with said bulk waste input means, for reducing the particle size of the infectious waste material;

a settling tank connected to said primary shredder for separating reduced waste material from waste residue, said settling tank capable of receiving fluid for filling to a predetermined fluid level sufficient to gravitationally separate the reduced waste material from waste residue;

a secondary rotary shear shredder, connected to said settling tank, which further reduces the particle size of the infectious waste material, said secondary shredder being in liquid communication with said settling tank and disposed below said fluid level of said settling tank;

a tertiary rotary shear shredder connected to said secondary shredder, which still further reduces the particle size of the infectious waste material, said tertiary shredder being in liquid communication with said secondary shredder and disposed below said fluid level of said settling tank;

a fluidized bed reactor disposed in a position to receive the infectious waste material from said settling tank, said fluidized bed reactor having a (1) diffusing means for releasing diluted ozone gas produced from an ozone generator into said fluidized bed reactor; (2) a venting means for relieving pressure within said fluidized bed reactor (3) recirculation port means to allow said waste slurry to be recirculated throughout said fluidized bed reactor; (4) a sample port means for drawing a sample of off gas from said fluidized bed reactor, said sample port being connected with an analyzing means; and (5) a discharge port means to allow said waste slurry to be removed from said fluidized bed reactor;

an ozone generator connected with said fluidized bed reactor, which continuously generates ozone gas at from about 1 to about 1.5 percent concentration by weight diluted in air at 10 psig., for about 5 to about 45 minutes;

an agitation means associated with said fluidized bed reactor;

an analyzing means associated with said fluidized bed reactor and connected with said ozone generator, wherein said analyzing means continuously monitors the amount of diluted ozone gas utilized in said fluidized bed reactor and meters the amount of diluted ozone gas generated from said ozone generator; and dewatering means associated with said fluidized bed reactor, which removes solid, disinfected waste material from liquid residue.

* * * * *

UNITED STATES PATENT AND TRADEMARK OFFICE
CERTIFICATE OF CORRECTION

PATENT NO. : 5,077,007
DATED : December 31, 1991
INVENTOR(S) : Erich H. Pearson It is certified that error appears in the above-identified patent and that said Letters Patent is hereby corrected as shown below:

In column 3, line 4, after "according to the present invention" insert --.--

In column 5, line 57, after "shredded waste" delete ",".

In column 6, line 31, after "gas phase or liquid oxygen" insert --.--.

In column 7, line 66, delete "aeruinosa" and insert therefor --aeruginosa--.

In column 7, line 67, delete "1.6'10$^5$" and insert therefor --1.6 x 10$^5$--.

In column 11, line 64, after "through a 3/4" insert --"--

In claim 1, column 13, line 9, after "(3) an agitation" insert --means associated with said tank means; and (4) an--.

In claim 9, column 13, line 64, after "means of said tank means" delete "is" and insert therefor --defines--.

In claim 15, column 16, line 4, before "rotary shear shredder" insert --primary--.

Signed and Sealed this

Twentieth Day of July, 1993

Attest:

MICHAEL K. KIRK

*Attesting Officer*   Acting Commissioner of Patents and Trademarks